(12) United States Patent
Kawai et al.

(10) Patent No.: US 6,666,876 B2
(45) Date of Patent: Dec. 23, 2003

(54) FORCEPS AND MANIPULATOR WITH USING THEREOF

(75) Inventors: Toshikazu Kawai, Chiyoda (JP); Kazutoshi Kan, Chiyoda (JP); Kouji Nishizawa, Tsuchiura (JP)

(73) Assignee: Hitachi, Ltd., Tokyo (JP)

( * ) Notice: Subject to any disclaimer, the term of this patent is extended or adjusted under 35 U.S.C. 154(b) by 127 days.

(21) Appl. No.: 09/790,633

(22) Filed: Feb. 23, 2001

(65) Prior Publication Data

US 2001/0021859 A1 Sep. 13, 2001

(30) Foreign Application Priority Data

Feb. 24, 2000 (JP) .................................. 2000-052239

(51) Int. Cl.[7] .............................................. A61B 17/44
(52) U.S. Cl. ........................ 606/205; 606/206; 606/208
(58) Field of Search ............................... 606/205, 206, 606/207, 208, 209; 74/490.06, 490.05; 901/29, 15, 28, 39

(56) References Cited

U.S. PATENT DOCUMENTS

| | | | | |
|---|---|---|---|---|
| 4,038,987 A | * | 8/1977 | Komiya | 606/142 |
| 4,511,305 A | * | 4/1985 | Kawai et al. | 414/735 |
| 4,721,116 A | * | 1/1988 | Schintgen et al. | 600/564 |
| 4,887,612 A | * | 12/1989 | Esser et al. | 600/564 |
| 5,241,968 A | * | 9/1993 | Slater | 600/564 |
| 5,697,949 A | * | 12/1997 | Giurtino et al. | 606/205 |
| 6,027,522 A | * | 2/2000 | Palmer | 606/205 |
| RE36,666 E | * | 4/2000 | Honkanen, deceased et al. | 606/205 |
| 6,394,998 B1 | * | 5/2002 | Wallace et al. | 606/1 |
| 6,409,727 B1 | * | 6/2002 | Bales et al. | 606/47 |
| 6,440,085 B1 | * | 8/2002 | Krzyzanowski | 600/564 |
| 6,461,310 B1 | * | 10/2002 | Palmer et al. | 600/567 |
| 6,497,651 B1 | * | 12/2002 | Kan et al. | 600/114 |

* cited by examiner

Primary Examiner—John J. Calvert
Assistant Examiner—Alissa L. Hoey
(74) Attorney, Agent, or Firm—Antonelli, Terry, Stout, & Kraus, LLP

(57) ABSTRACT

A forceps, comprising: a pair of forceps members, being able to open or close at one end, so as to put an object between them, and being supported at the other end thereof; a driving wire for transferring tension thereon to the forceps members for bringing them to open and close; and a driver portion for giving the tension onto the driving wire, wherein: one of the forceps members is built up with a member (A) 41, being able to open or close at one end, so as to put the object between them, while being supported to freely rotate at the other end, and the other member with a member (B) 42, being able to put the object between them, but being supported fixedly at the other end; the driving wire 44 is wound around a rotary portion at the other end of the member (A) 41, and a portion of the wound portion thereof is fixed onto the rotary portion; and a tension for open and close operation is given from the driver portion to one end of the driving wire 44. Also, this forceps is inserted into inside of a manipulator, to be used therewith.

11 Claims, 14 Drawing Sheets

FORCEPS AND MANIPULATOR WITH USING THEREOF

BACKGROUND OF THE INVENTION

1. Field of the Invention

The present invention relates to a forceps and a manipulator with using thereof, and in particular, relates to a forceps and a manipulator with using thereof, which can be operated in a narrow operating space or room.

2. Description of Prior Art

For aiming early medical treatment and recovery from an illness, a surgery assistance system is expected for assisting surgery or operation (low-invasive surgery) that is short in time and gives no injury upon normal organizations other than the diseased part, as far as possible. With that low-invasive surgery, it can be expected to reduce a load upon a doctor when conducting the surgical operation, and medical expenses, as well. Further, such the assistance of the doctor can cover the difference between the individuals, and in addition thereto, it enables the surgical operation of a diseased part, at which surgical treatment was difficult up to this day. For example, in the low-invasive surgery, in particular when aiming brain surgery, the following operations are required to be performed in a narrow operating space; such as grasp and/or separation of a blood vessel and/or a nerve, an incision and/or removal of a tumor, etc. In those minute surgical operations, a fine or microscopic handling function is important, therefore a surgical instrument or machine, such as a minute forceps, etc., is necessary, which is small-sized and can finely perform open-close operation within the operating space.

The minute forceps of the conventional art, driven by a push-rod in the driving method thereof, performs the open and close through push-pull operation by means of a wire having a strong rigidity or stiffness. In more details, with the push-rod driving method, the movement in front and behind of the rod is transferred to a treatment part through a link, thereby to make the open and close operation thereof. Each part constructing the link is connected by means of a joint, such as a pin, etc. When repeating the open and close operation of the manipulator by the movement in front and behind of the rod, forces are repetitively transferred to a joint portion in different directions accompanying with the movement in back and forth, therefore the joint portion is fixed firmly through welding, etc. Namely, the consideration is not paid upon rinsing and/or sterilization by a unit of the constituent parts thereof.

The minute forceps aimed to be operated within the narrow operating space, for example in the surgical operation under an endoscope, is already described in, for example, Japanese Patent Laying-Open No. Hei 8-103450 (1996), and Japanese Patent Laying-Open No. Hei 11-113919 (1999), etc.

In such the surgery assistance system for assisting the low-invasive surgery, a plural number of manipulators, each attached with the minute forceps or the like, are used together with the endoscope, being tied with in a bundle. For performing the fine surgical operation with the bundle of the manipulators and the endoscope, it is necessary to enlarge an operable angle at the tip of the manipulator, and the more close to zero (0) degree the curvature radius of a swing portion at the tip, the finer the operation available. Accordingly, the driving force must be transferred to the minute forceps attached to the tip of the manipulator, but without losses, even when the manipulator is bent at the swinging joint thereof.

For example, in the conventional minute forceps using the push-rod mechanism, the minimum curvature radius is about 20 mm, being necessary for protecting the rod from transferring the driving force from buckling thereof, therefore it is impossible to reduce the curvature radius less than that, no more.

Also, when trying to obtain the small-sizing in the tip portion of the forceps, the number of constituent parts comes to large, it is impossible to ensure the thickness thereof necessary for maintaining the mechanical strength thereof, and further it needs an assembling technology of high accuracy for assembling a large number of links included therein.

Also, with the manipulator mechanism of the conventional push-rod driving method, a pin constructing the link mechanism is fixed through the welding, etc., upon the method thereof, therefore the constituent parts are not detachable. Namely, no such the consideration is not taken into, necessarily, that they can be detached from the joint portion thereof, to be rinsed and/or sterilized by the unit of the constituent part.

SUMMARY OF THE INVENTION

An object, according to the present invention, is to provide a forceps and a manipulator with using thereof, with which the tension of a driving wire, transferred to the forceps for open and close operation thereof, can be maintained at a constant, even when it is bend at a small curvature radius.

And, further other object, according to the present invention, is to provide a forceps and a manipulator with using thereof, which can be disassembled detachably into a plural number of the constituent parts constructing the manipulator mechanism, thereby obtaining good washability.

For achieving the above-mentioned object, according to the present invention, there is provided a forceps, comprising: a pair of forceps members, being able to open or close at one end, so as to put an object between them, and being supported at the other end thereof; a driving wire for transferring tension thereon to said forceps members for bringing them to open and close; and a driver portion for giving the tension onto said driving wire, wherein: one of said forceps members is built up with a member (A), being able to open or close at one end, so as to put the object between them, while being supported to freely rotate at the other end, and the other member with a member (B), being able to put the object between them, but being supported fixedly at the other end; the driving wire is wound around a rotary portion at said other end of the member (A), and a portion of the wound portion thereof is fixed onto said rotary portion; and the tension for open and close operation is given from said driver portion to one end of the driving wire.

In more details, according to the present-invention, in the forceps as defined in the above, wherein the position where said driving wire is fixed onto the rotary portion is set at a position, so that the driving wire remains on-the rotary even if the member (A) opens at 90 degree to the member (B).

For achieving the above-mentioned object, according to the present invention, there is also provided other structure of a forceps, comprising: a pair of forceps members, being able to open or close at one end, so as to put an object between them, and being supported at the other end thereof; a driving wire for transferring tension thereon to said forceps members for bringing them to open and close; and a driver portion for giving the tension onto said driving wire, wherein: one of said forceps members is built up with a member (A), being able to open or close at one end, so as to put the object between them, while being supported to freely rotate at the other end, and the other member with a member (B), being able to put the object between them, but being supported fixedly at the other end; the driving wire is wound around a rotary portion at said other end of the member (A), and a portion of the wound portion thereof is fixed onto said rotary portion; and the driving wire is connected to the driver portion passing through an inside of a sheath.

For achieving the above-mentioned object, according to the present invention, there is further provided other structure of a forceps, comprising: a pair of forceps members, being able to to put an object between them, and being supported at the other end thereof; a driving wire for transferring tension thereon to said forceps members for bringing them to open and close; and a driver portion for giving the tension onto said driving wire, wherein: one of said forceps members is built up with a member (A), being able to open or close at one end, so as to put the object between them, while being supported to freely rotate at the other end, and the other member with a member (B), being able to put the object between them, but being supported fixedly at the other end; the driving wire is wound around a rotary portion at said other end of the member (A), and a portion of the wound portion thereof is fixed onto said rotary portion; the driving wire is connected to the driver portion passing through an inside of a sheath, in which an elastic member lies therebetween; at a position of the elastic member is provided a means for separating the driving wire from an inner wall of the sheath; and the tension for open and close operation is given from the driver portion to the driving wire.

In more details, according to the present invention, in the forceps as defined in the above, wherein the means for separating said driving wire from the inner wall of the sheath is so constructed that, the driving wire passes through a bored sphere, on which a bore is formed, and a portion of the bored sphere comes to a hollow portion of the elastic member.

For achieving the above-mentioned object, according to the present invention, there is further provided other structure of a forceps, comprising: a pair of forceps members, being able to open or close at one end, so as to put an object between them, and being supported to freely rotate at the other end thereof, wherein: a joint portion of said pair of forceps members, being supported to freely rotate at the other end thereof, is constructed to be detachable.

In more details, according to the present invention, in the forceps as defined in the above, wherein the pair of forceps members are fitted at the joint portions thereof, through a lock and fitting structure by means of a pin, in said detachable structure.

In more details, according to the present invention, in the forceps as defined in the above, wherein the pair of forceps members are fitted at the joint portions thereof, through a structure by means of a pin and a stop ring, in said detachable structure.

For achieving the above-mentioned object, according to the present invention, there is further provided other structure of a forceps, comprising: a pair of forceps members, being able to open or close at one end, so as to put an object between them, and being supported to freely rotate at the other end thereof, wherein: between said forceps member, one forceps members is built up with a member (A), being able to open or close at one end, so as to put the object between them, while being supported to freely rotate at the other end; and the other forceps member with a member (B), being able to put the object between them, but being supported fixedly at the other end; and said member (B) is divided along an axis direction from a top end to a back portion on a non-holding side thereof, and the member (A) is put between the both members divided, so as to hold the object therewith.

In more details, according to the present invention, in the forceps as defined in the above, wherein said divided member (B) can be fixed by inserting a tube from an outside.

For achieving the above-mentioned object, according to the present invention, there is further provided other structure of a forceps, comprising: a pair of manipulator members, being able to open or close at one end, so as to put an object between them, and being supported to freely rotate at the other end thereof, wherein: between said forceps member, one forceps member is built up with a member (A), being able to open or close at one end, so as to put the object between them, while being supported to freely rotate at the other end; and the other forceps member with a member (B), being able to put the object between them, but being supported fixedly at the other end; and said driving wire is detachably connected to a rotary portion of said member (A) on a non-holding side thereof, through a fixing member.

In more details, according to the present invention, in the forceps as defined in the above, wherein a projection is formed on said rotary portion or a fixed member, thereby fixing the driving wire thereon.

In more details, according to the present invention, in the forceps as defined in the above, wherein a projection or a recess portion is formed on said member (A) while a recess portion or a projection on the fixed member, thereby fixing the fixed member onto the member (B).

For achieving the above-mentioned object, according to the present invention, there is further provided other structure of a forceps, comprising: a pair of manipulator members, being able to open or close at one end, so as to put an object between them, and being supported to freely rotate at the other end thereof, wherein: between said forceps member, one forceps member is built up with a member (A), being able to open or close at one end, so as to put the object between them, while being supported to freely rotate at the other end; and the other forceps member with a member (B), being able to put the object between them, but being supported fixedly at the other end; and a joint portion of said pair of forceps members, the other ends of which are rotatably supported, is constructed to be a detachable; and said driving wire is detachably fixed onto a rotary portion of said member (A) on a non-holding side thereof, through a fixing means.

For achieving the above-mentioned object, according to the present invention, there is further provided other structure of a forceps, comprising: a pair of treatment members, being able to open or close at one end, so as to put an object between them, and being supported to freely rotate at the other end thereof; a rod for transferring forces of movement in back and forth to said treatment members, so as to open and/or close them; and a link mechanism and a connector for connecting between those treating members and the rod, wherein: the joint portion connecting between said treatment members and the link mechanism has a detachable structure.

In more details, according to the present invention, in the forceps as defined in the above, wherein the joint portion has a fitting structure between a projection and a bore in said detachable structure, and the fitting structure remains when they are at an angle being equal to or greater a predetermined value.

For achieving the above-mentioned object, according to the present invention, there is further provided other structure of a forceps, comprising: a pair of treatment members, being able to open or close at one end, so as to put an object between them, and being supported to freely rotate at the other end thereof; a rod for transferring tension to the treatment members, so as to open and/or close them; and a link mechanism and a connector for connecting between those treating members and the rod, wherein: the joint portion connecting between said treatment members and the link mechanism has a detachable structure.

In more details, according to the present invention, in the forceps as defined in the above, wherein said connector be divided along with an axial direction thereof, and said link mechanism and said rod are fixed at end portion thereof by means of the divided connector.

And, according to the present invention, also for achieving the above-mentioned object, there is provided a manipulator, with using a forceps, comprising: a pair of forceps members, being able to open or close at one end, so as to put an object between them, and being supported at the other end thereof; a driving wire for transferring tension thereon to said forceps members for bringing them to open and close; and a driver portion for giving the tension onto said driving wire, wherein said manipulator further comprising: a driving wire for performing a swing operation at a tip there; and a driver portion for giving a tension to the driving wire, wherein: the forceps is inserted in this manipulator; in this forceps, between said forceps members, one forceps member is built up with a member (A), being able to open or close at one end, so as to put the object between them, while being supported to freely rotate at the other end; and the other forceps member with a member (B), being able to open or close at one end, so as to put the object between them, but being supported fixedly at the other end; the driving wire is wound around a rotary portion at said other end of the member (A), and a portion of the wound portion thereof is fixed onto said rotary portion; and the tension for open and close operation is given from said driver portion to one end of the driving wire.

For achieving the above-mentioned object, according to the present invention, there is further provided other structure of a manipulator, with using a forceps, comprising: a pair of forceps members, being able to open or close at one end, so as to put an object between them, and being supported at the other end thereof; a driving wire for transferring tension thereon to said forceps members for bringing them to open and close; and a driver portion for giving the tension onto said driving wire, wherein said manipulator further comprising: a driving wire for performing a swing operation at a tip there; and a driver portion for giving a tension to the driving wire, wherein: the forceps is inserted in this manipulator; in this forceps, between said forceps members, one forceps member is built up with a member (A), being able to open or close at one end, so as to put the object between them, while being supported to freely rotate at the other end; and the other forceps member with a member (B), being able to put the object between them, but being supported fixedly at the other end; the driving wire is wound around a rotary portion at said other end of the member (A), and a portion of the wound portion thereof is fixed onto said rotary portion; and the driving wire is connected to the driver portion passing through an inside of a sheath, in which an elastic member lies therebetween; at a position of the elastic member is provided a means for separating the driving wire from an inner wall of the sheath; and the tension for open and close operation is given from the driver portion to the driving wire.

For achieving the above-mentioned object, according to the present invention, there is further provided other structure of a manipulator with using a forceps, comprising: a pair of forceps members, being able to open or close at one end, so as to put an object between them, and being supported at the other end thereof; a driving wire for transferring tension thereon to said forceps members for bringing them to open and close; and a driver portion for giving the tension onto said driving wire, wherein a joint portion of said pair of forceps members, being supported to freely rotate at the other end thereof, is constructed-to be detachable.

DETAILED DESCRIPTION OF PREFERRED EMBODIMENT(S)

Hereinafter, embodiments according to the present invention will be fully explained by referring to the attached drawings.

Figure 1:
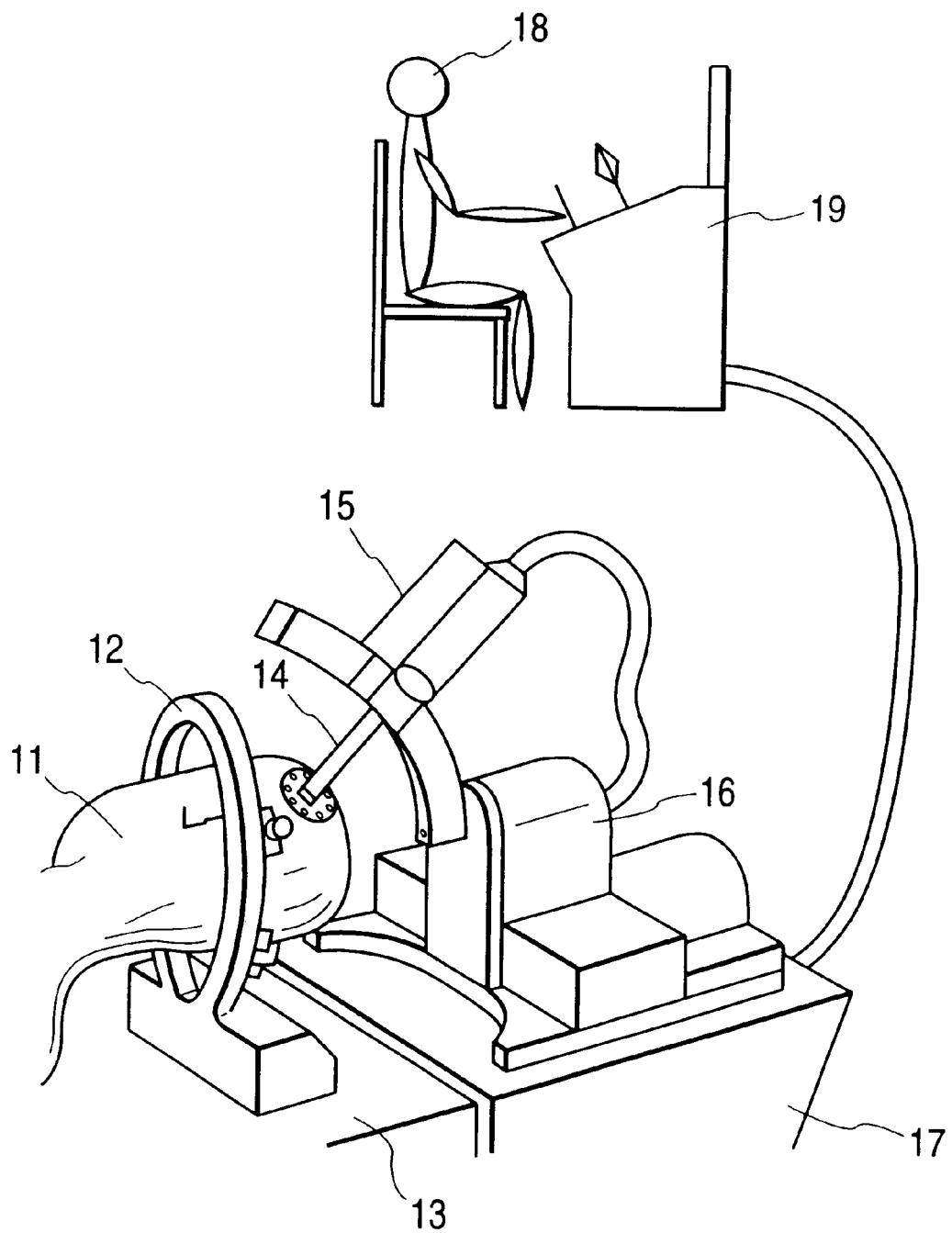
FIG. 1 is a view of the structure of a surgical operation assistance system for the low-invasive surgical operation.
Figure 2:
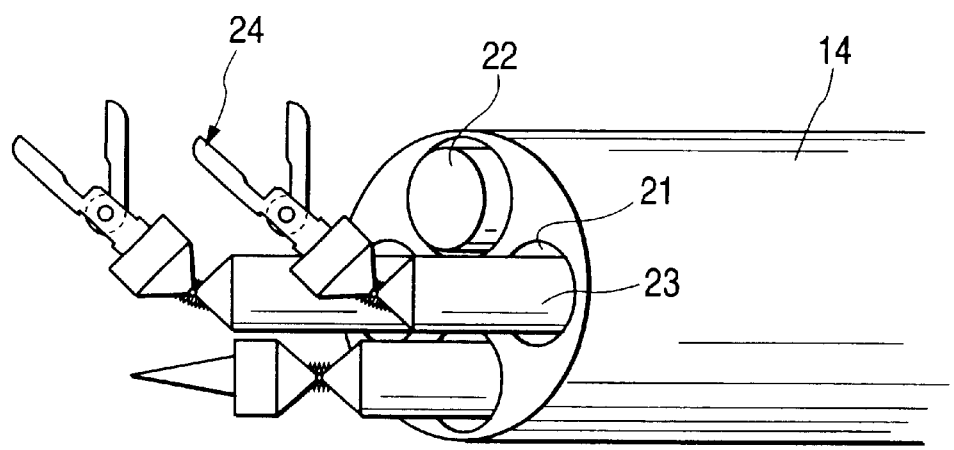
FIG. 2 is a partial view of the surgical operation assistance system, bundling the manipulator according to the present invention together with an endoscopes.
Figure 3:
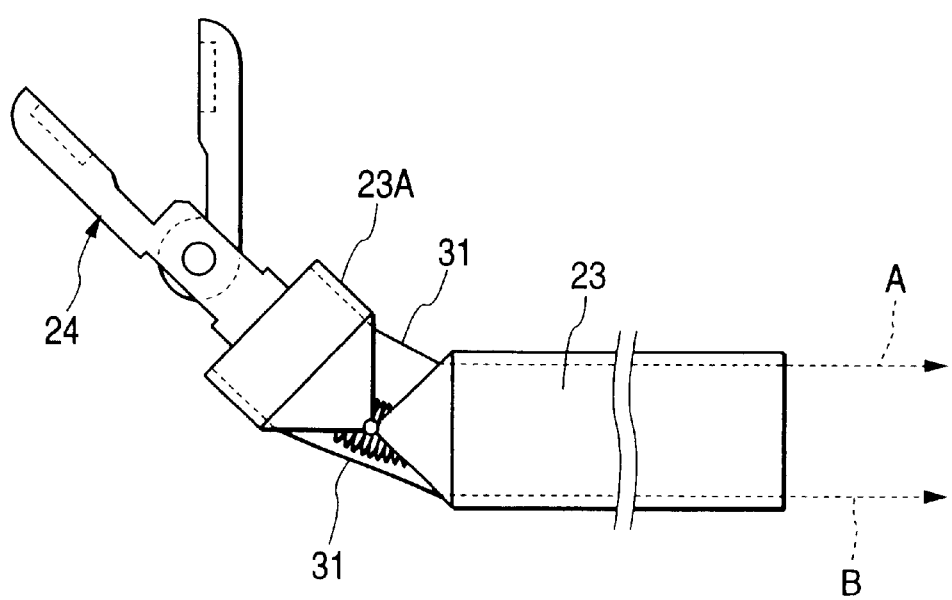
FIG. 3 is a view for showing the manipulator according to the present invention, and a forceps inserted inside the manipulator.

FIG. 1 shows a surgical operation assistance system for the low-invasive surgical operation, in particular aiming the surgery of a brain; and FIG. 2 shows a partial view of the surgical operation assistance system, in which the manipulator is bundled together with an endoscopes. FIG. 3 shows the manipulator and a forceps inserted inside the manipulator.

In the FIG. 1, a head 11 of a patient is fixed on an operating table 13 by means of a head fixing frame 12. An insertion pipe 14, which is inserted into the head 11, comprises a guide opening 21, as shown in the enlarged view of the FIG. 2, and inside the guide opening 21 are guided or inserted an endoscope 22 and plural pieces of manipulators 23, being bundled as one, thereby constructing an insertion portion. To the manipulator 23 is attached a forceps 24. This manipulator 23 is driven by a driver portion 15, which is attached onto a holder apparatus 16. The holder apparatus 16 is fixed onto a holder base 17. An operator 18 (i.e., a doctor) performs the surgical operation by operating the manipulator 23 through an operation input apparatus 19.

In the FIG. 3, a tip portion 23A of the manipulator 23 makes a swing operation by means of a driving wire 31, and in inside of the manipulator 23 is formed a hollow guide opening for inserting a forceps 24 therein. And they are constructed so that, the tip portion 23A makes the swing operation upward in the figure when the driving wire 31 is pulled up in the direction of an arrow A through the driver portion 15, while the tip portion 23A swings downward when the wire 31 is pulled up in the direction of an arrow B.

Figure 4A:
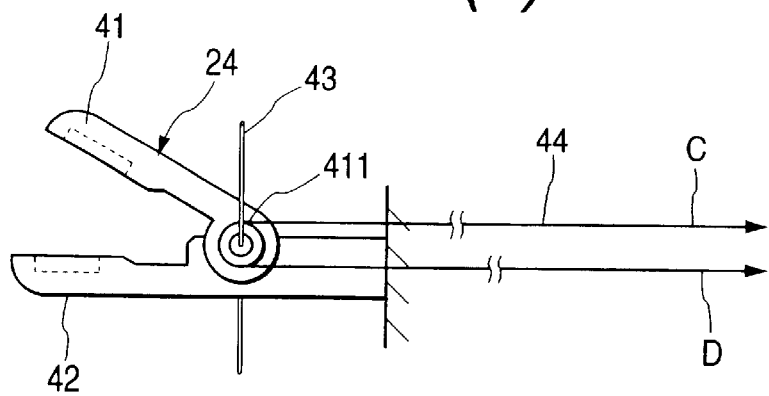
FIG. 4 (*a*) is a view for showing main structure of a forceps of a one-side driving method and for explaining a driving principle thereof, FIG. 4 (*b*) a view for explaining a member thereof, and FIG. 4 (*c*) a view for showing main structure of a forceps of a both-side driving method and for explaining a driving principle thereof.
Figure 4B:
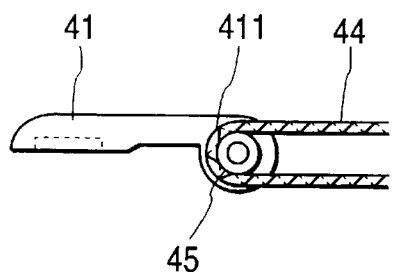
Figure 4C:
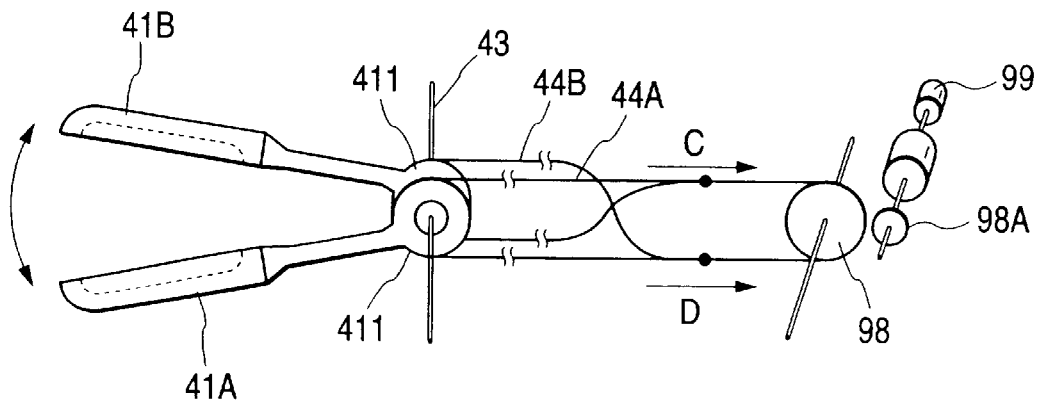

FIGS. 4 (a) to (c) show main structure of the forceps, and explain the driving principle thereof.

In the FIG. 4 (a) showing of the one-side driving method, the forceps is constructed with: a member (a movable forceps member) 41, putting an object therebetween by opening or closing at one end thereof and being rotatably supported at the other end; a member (a fixed forceps member) 42, being supported under the condition that both sides thereof are fixed, i.e., with no open and close operation, nor rotation; a joint 43 for bringing the rotary center of the member 41 to be coincident with the support center of the member 42; and a driving wire 44 for transferring a tension to the forceps to open and close. A rotary portion 411 of the member 41 is made in a form of a circuit, on a peripheral portion thereof, and on the rotary portion 411, as shown in the FIG. 4 (b), is fixed the driving wire 44, over nearly equal a quarter (¼) of an outer periphery thereof. The driving wire 44 is fixed, for example, through a bonding by an adhesive and/or a resin, or a connection by a caulking, etc., and is wound around the outer periphery of the rotary portion 411 over a range of 180 degree (a half-round). The position where the driving wire 44 is fixed onto the wire fixing portion 45 is so selected that, the driving wire 44 will not be separated from the fixing portion 45 by the wire tension (a portion of hatching), even when the member 41 is opened at a right angle (90 degree) with respect to the member 42; namely, the position where it is in contacts with the fixed portion 45. After bringing the rotary center of the rotary portion 411 into line with the support center of member 42, the joint 43 is inserted (the portion being connected by a pin, which will be mentioned later).

FIG. 4 (c) shows the forceps of the both-side driving method, and it comprises: two (2) pieces of movable forceps members 41A and 41B (indicated by only a reference numeral "41" when they are referred collectively, and so forth); and two (2) pieces of driving wires 44A and 44B (indicated by only a reference numeral "44" when they are referred collectively, and so forth), wherein the driving wires 44A and 44B are wound around the rotary portions 411, respectively. Further, reference numerals 98 and 98A indicate a pulleys, and 99 a driving motor.

With this both-side drive method, the movable forceps members 41 are operated to open and close by giving the tension to the driving wires 44 in the direction of either an arrow C or D. Namely, on the lower side of the driving wire 44A shown in the drawing is connected or bonded an end of the driving wire 44B, while on the upper side of the driving wire 44A shown in the drawing is connected or bonded the other end of the driving wire 44B, so as to cross over. Accordingly, the members 41A and 41B rotate to open when the tension is given to the driving wires 44 into the direction of the arrow D, while rotate in the direction to close when the tension is given in the direction of the arrow C, thereby achieving the hold operation by always giving the tension thereto. Due to this, comparing to the one-side drive method, further members are necessary for supporting the members 41A and 41B by a pin, separately, therefore the number of parts thereof is increased.

Figure 5:
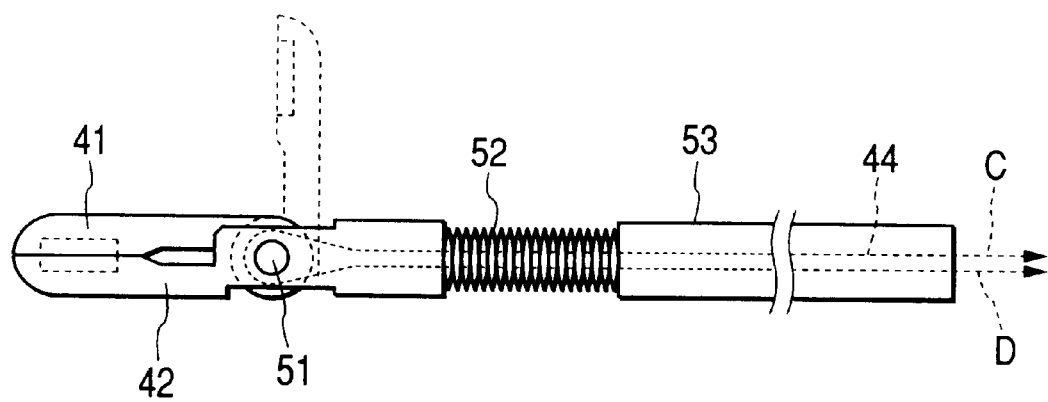
FIG. 5 is an outlook view of the forceps according to the present invention.

FIG. 5 is an outlook view of the tip portion of the forceps of the one-side driving method, according to the present embodiment.

The forceps is constructed with: a fixed member 42; a movable member 41, a driving wire 44, a pin 51 as a joint 43, an elastic member 52, and a sheath 53. The sheath 53 is connected through the elastic member 52, and this elastic member 52 is hollow inside. In the inside of this, the driving wire 44 passes through, and this is able to protect the wire from buckling caused when it is bent, by using a spring having a high elasticity. A material having a less friction is used inside the sheath 53, and then the driving wire 44 shifts within the sheath 53 smoothly. Therefore, as was mentioned in the above, when the driving wire is pulled in the direction C, the member 41 is shifted as indicated by a broken line, thereby opening the forceps, while, when being pulled in the direction of the arrow D, the forceps is closed as shown by a solid line.

With adopting such the one-side driving method as was mentioned in the above, the member 42 is not driven even if an important organ lies within the operating space, therefore if that portion is disposed on the side of the organ, it is possible to perform the hold operation through driving of the member 41, but without giving injury on the organ. Also, when trying to hold the object, bringing a holding surface of the member 42 to be contact with the object can avoid a failure in the holding thereof.

Figure 6A:
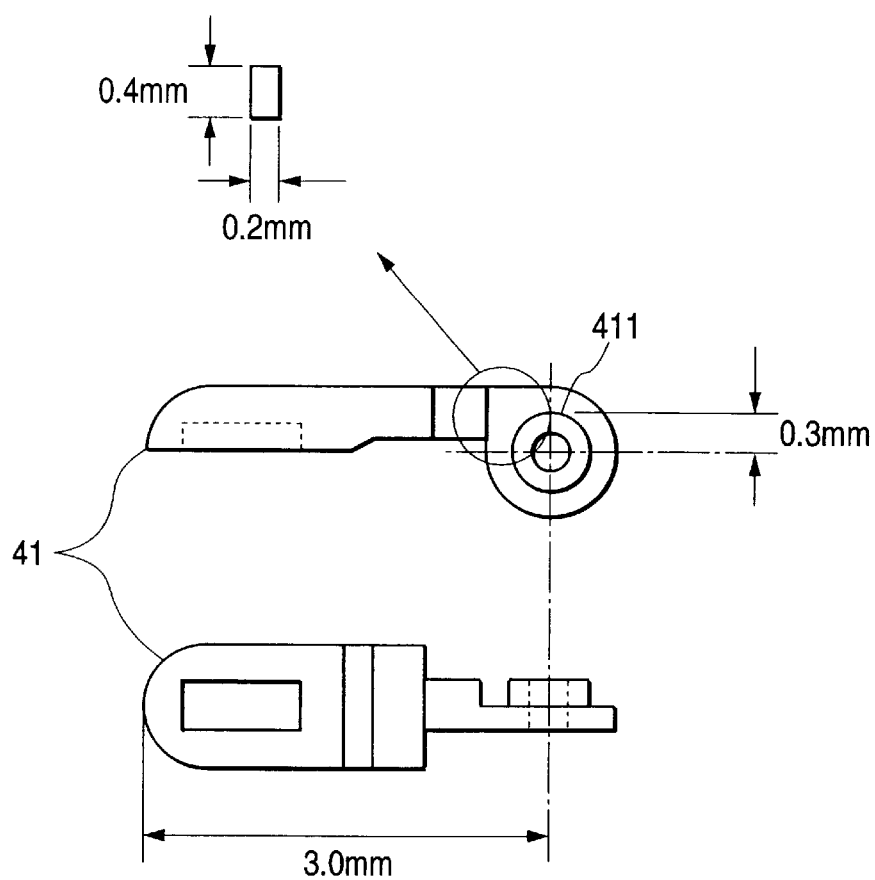
FIGS. 6 (*a*) and (*b*) are detailed views of parts of the forceps shown in the FIG. 5.
Figure 6B:
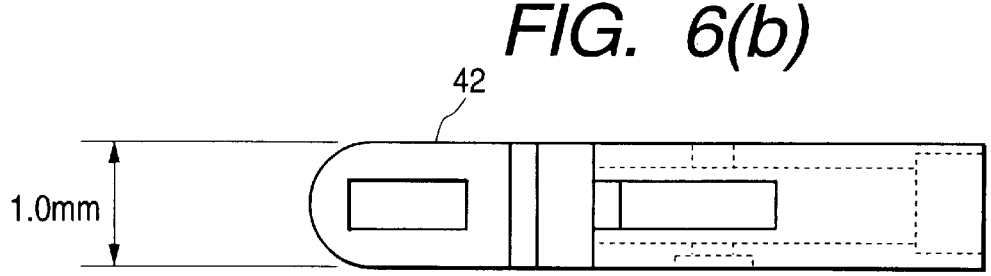
Figure 6B:
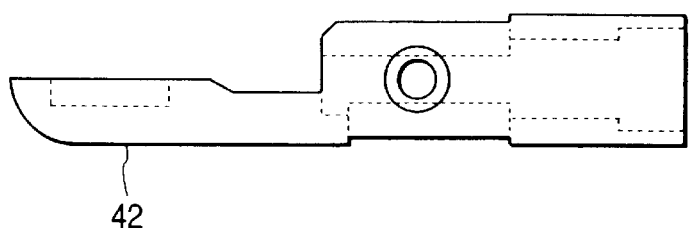

In FIG. 6 (a) is shown the detailed portion of the movable forceps member 41, and in FIG. 6 (b) the portion of the fixed forceps member 42.

The same figures show an example, which is designed to be 1 mm in the diameter of the forceps under the condition it is closed, and to be 100 gf or more in the holding force by the forceps. For example, on an outer periphery of the rotary portion 411 of the member 41 is disposed and/or fixed the driving wire 44, and the thickness at that portion is assumed to be 0.2 mm, the size in the direction of length be 0.4 mm, the length from the rotary center of the rotary portion 411 to the portion where the driving wire 44 is fixed be 0.3 mm, and the length to the tip of the forceps be 3 mm. Also, it is assumed that the driving wire used herein has a strength of 3.3 kg.

Assuming that the member 41 be a beam having a rectangular cross-section of a width: 0.2 mm and a height: 0.4 mm, and a length: 3 mm, a rigidity is obtained at the tip of the forceps. A cross-sectional secondary moment to a neutral axis can be obtained by the following equation:

$$I = \frac{bh^3}{12} \quad (1)$$

Where, "I" indicates the cross-sectional secondary moment: $mm^4$, "b" the width of the neutral axis: mm, and "h" the height: mm, respectively. Obtaining the secondary moment of the member 41, from the above equation (1), it is $I=1.067\times10^{-3}$ $mm^4$, by inserting b=0.2 mm, and h=0.4 mm. Also, the maximum deflection of the beam can be obtained from the following equation:

$$\ddot{a}_{max} = \frac{Wl^3}{3EI} \quad (2)$$

Where, "ämax" indicates the maximum deflection: mm, "W" the concentrated load at a free end: kg, "1" the length of the beam: mm, "E" an elastic coefficient: $kg/mm^2$, and I the cross-sectional secondary moment: $mm^4$, respectively.

By restricting the maximum deflection at the tip of the member 41, it is possible to obtain the concentrated load, i.e., the rigidity at the tip of the forceps. Then, obtaining the rigidity when the member 41 is made of using SUS304, the following can be obtained from the equation (2) mentioned above: ämax=0.25 mm, 1=3 mm, $E=19\times10^3$ $kg/mm^2$, and then W=0.57 kg.

The maximum endurable tension of the driving wire 44 comes to be 1.6 kg when applying 2 into a safety factor. The torque of the forceps can be obtained from the following equation:

$$T=Fr \quad (3)$$

Where, "T" indicates the torque: kgm, "F" a force for the rotation: kg, and "r" a distance between the force F and the rotation axis: m. obtaining the force at the tip of the member through a torque conversion, it is F=1.6×0.3/3.0=0.16 kg, from the equation (3) mentioned above. This value is larger than that of the rigidity of the member 41, therefore the maximum holding force is 160 g so far as the driving wire 44 is not broken. Also, if making the rigidity small but not be less than the wire strength, the further small-sizing can be obtained.

Figure 7:
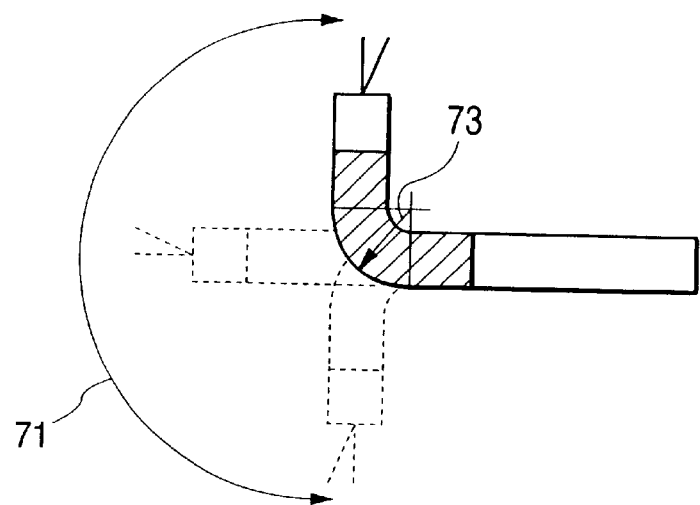
FIG. 7 is an explanatory view on a movable swinging region of the forceps shown in the FIG. 3.
Figure 8:
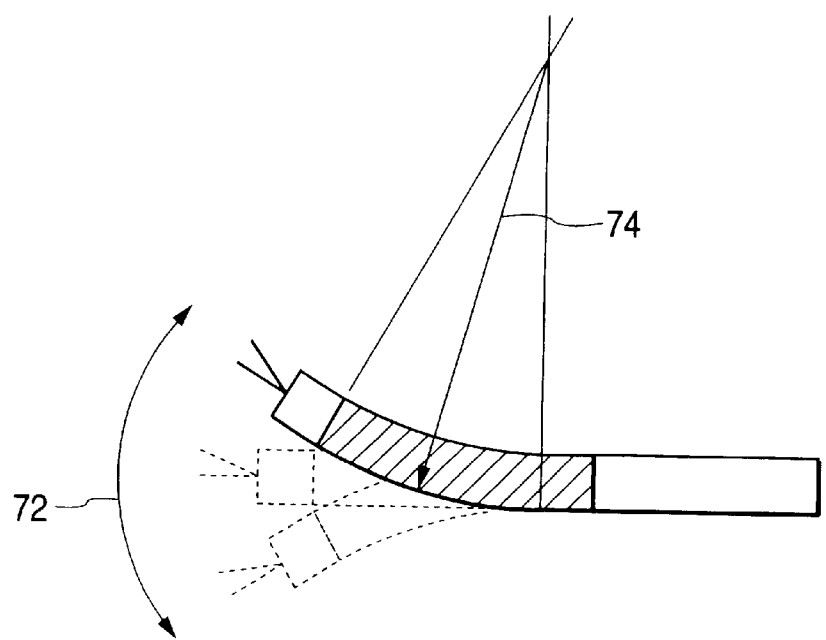
FIG. 8 is an explanatory view on a movable swinging region of the forceps according to the conventional art.

In FIGS. 7 and 8 are shown the movable regions of swinging and the curvature radii, in the forceps according to the present invention and the conventional art, in comparison therewith. In particular, the FIG. 8 shows the movable region of swinging and the curvature radius in the forceps of the conventional art.

The FIG. 7 shows those obtained according to the present invention, wherein a reference numeral 71 indicates the movable region of swing of the forceps, i.e., the region defined by a solid line and a broken line in an upper and lower portions of the figure, and 73 the curvature radius, shown by an arrow of solid line in the figure. The FIG. 8 shows those of the conventional art, in the same manner, and a reference numeral 72 indicates the movable region of swing for the forceps, and 74 the curvature radius.

As be apparent from the figures, with the forceps obtained according to the present invention, it is possible to make the movable region of swing larger, and the curvature radius smaller, comparing to those of the conventional art. A reason of this lies in that, though the driving force for open and close is transferred by the push-pull operation of the rod in the push-rod mechanism of the conventional forceps, on the contrary, the driving force for open and close is transferred by a pulling operation of the driving wire 44 in the forceps of the present embodiment. Therefore, the buckling of the drive wire has no relationship with the transfer of the driving force, and due to the fact that it is possible to use a wire having the rigidity or stiffness smaller than that of the rod which is used in the forceps of the conventional art. Accordingly, the curvature radius 73 in the forceps according to the present embodiment can be made to be smaller, comparing to the curvature radius 74 in the forceps of the conventional art. In the FIG. 7, assuming that the curvature radius 74 is 20 mm, for example, the curvature radius 73 is 1 mm. Therefore, the open and close operation can be performed with making the curvature radius 73 small, thereby enabling the more minute open and close operation.

Figure 9:
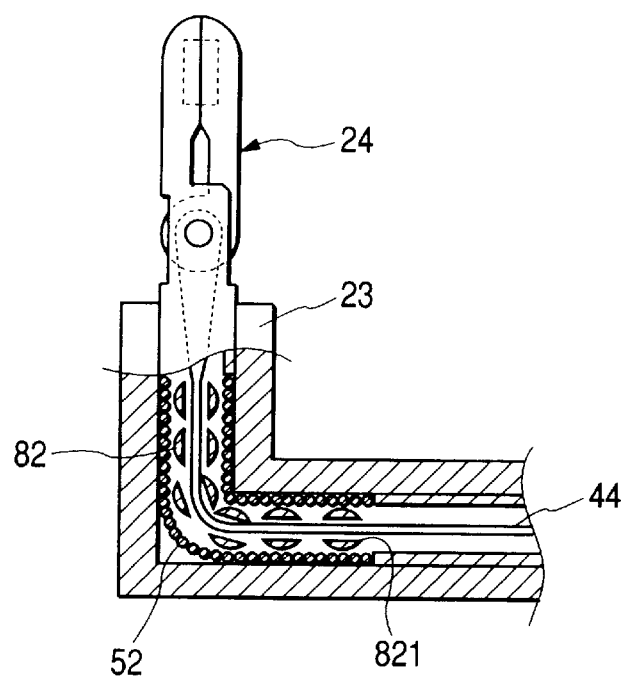
FIG. 9 is a view for showing a route of a wire for use of driving the forceps in-the manipulator shown in the FIG. 3.

FIG. 9 shows the manipulator, in which is provided a means for separating the driving wire from an inner wall of the sheath, thereby maintaining the tension at constant, on the driving wire for making the forceps open and close, therefore it is also possible to keep the holding force obtained therewith at a constant.

Figure 10:
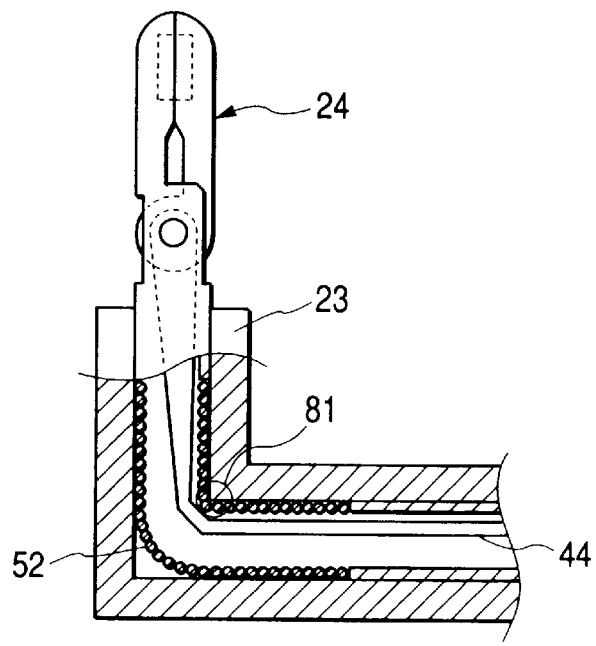
FIG. 10 is a view for showing a route of a wire for use of driving the forceps in the manipulator according to the conventional art.

The FIG. 9 is the view for showing a route of the driving wire in the present embodiment, while the FIG. 10 is the view for showing a route of the driving wire in the conventional art.

Even in a case where the manipulator 23 is bent, and accompanying to this, the elastic member 52 is bent, there is a necessity that the tension is transferred to the forceps without losses. As shown in the FIG. 10, since the driving wire 44 tries to pass through the minimum distance in a bent portion 81 of the elastic member 52, a large deflection occurs in the driving wire 44 accompanying with the bent of the manipulator 23. According to this, since a large friction is generated in the bent portion 81, it is impossible to transfer the holding force to the forceps, so that it performs the open and close operation correctly, thereby needing the tension much more.

According to the present embodiment, for avoiding such the inconvenient or disadvantageous friction as was mentioned in the above, as shown in the FIG. 9, a bored sphere 82 is used, on which a bore is opened in the center thereof.

Namely, the driving wire 44 is passed through the bore 821 formed on the sphere 82 (preferable to have a small friction coefficient), and they are positioned so that the bored sphere 82 comes in the hollow portion of the elastic member 52. With doing so, because of the existence of the bored sphere 82 even if the elastic member 52 is bent, the driving wire 44 is separated from the inner wall of the bent portion 81, thereby bringing the curvature radius to be large. Namely, because of the fact that the driving wire passes through almost the central portion of the bent portion 81, the curvature radius thereof comes to be large, thereby occurring no small deflection therein. Also, the driving wire moves sliding on the smooth surface inside the bore 82, therefore the loss due to the friction is lowered.

Accordingly, the tension thereof as the driving force does not change when the driving wire is bent, therefore it is possible to maintain the holding force of the forceps at constant. However, with the bored sphere 82, in particular the diameter thereof, it is preferable to pay consideration so that, the driving wire 44 passes through almost the center of the hollow portion of the elastic member 52 when it is bent.

Also, as other structures for letting the driving wire 44 to pass through the center of the elastic member 52, there may be one, in which the center of the hollow portion of the elastic member is shifted from the center of the elastic member, for example, the driving wire 44 passes through while the thickness of the inner wall is increased on the elastic member 52, at the position which comes to inside when it is bent, and one, in which the inner diameter is made thin in the hollow portion of the elastic member. Further, in a case where it is not driven by manual operation, but with an automatic driving through a motor, and if the driving wire does not pass through the center of the elastic member, there may be also other structure, in which the tension is given by taking the deflection following when it is bent into the consideration, on a software.

Figure 11A:
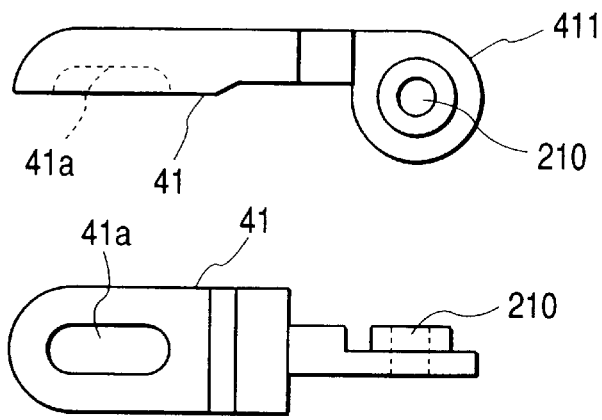
FIGS. 11(*a*) to (*c*) are views for showing a fitting structure relating to the forceps of the present invention.
Figure 11B:
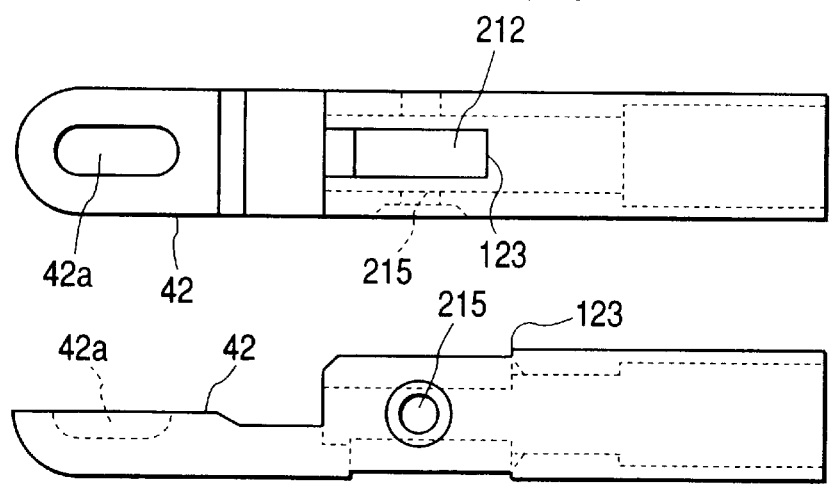
Figure 11C:
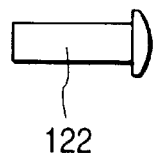

FIGS. 11 (*a*) to (*c*) show further other embodiment of the forceps, according to the present invention.

The FIG. 11(*a*) shows, in particular, a side view of a member of the movable forceps in an upper side of the drawing, while a front plan view thereof in a lower side thereof, the FIG. 11 (*b*) a front plan view of a member of the fixed forceps in an upper side while a side view thereof in a lower side thereof, and the FIG. (*c*) a side view of the pin for use as the joint. In the present embodiment, a pin 122 having a fitting (lock and fitting) structure is used as the joint 43 shown in the FIG. 4.

On the member 42 shown in the FIG. 3 (*b*), there are formed a bore 212, in which the rotary portion 411 of the member 41 is inserted, and a stage-like stopper 123 for preventing the member 41 from being opened at an angle being equal to or greater than 90 degree. For obtaining the fitting structure, namely the lock and fitting structure, the pin 122 must be made up at a tolerance, for example, h6 (JIS standard, and so forth), by taking the engagement with the bore 215 on the member 43 into the consideration. In this instance, the tolerance of the bore 215 is set to H6, for example. The tolerance of a bore 210 for use of the join, which is formed on the member 41 is set to H7, for example, so that no looseness is caused due to the repetitive hold operations thereof and that the member 41 can rotate smoothly. Namely, it is of the structure for supporting the member 41 on the member 42 rotatably, but without using such as a stop ring or the like.

According to the present embodiment, by applying the fitting or engagement structure by means of the pin, it is possible to disassemble and/or assemble the fixed manipulator member and the movable manipulator member, with ease, thereby enabling easy rinsing and/or sterilization thereof.

Figure 12A:
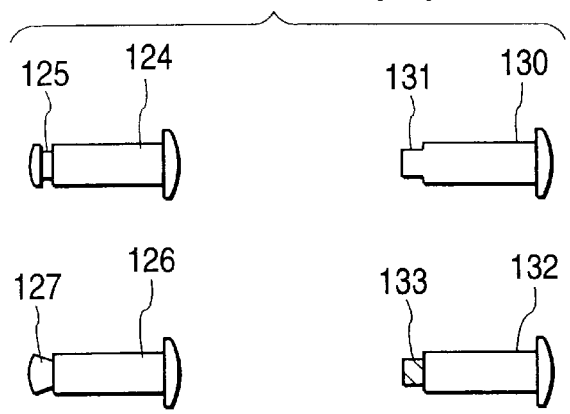
FIGS. 12 (*a*) and (*b*) are views for showing the structure of pins relating to the forceps of the present invention FIGS. 13 (*a*) to (*c*) are views for showing other embodiment of the forceps according to the present invention.
Figure 12B:

FIGS. 12 (*a*) and (*b*) show other embodiment applying the structure other than the fitting or engagement structure mentioned above.

FIG. 12 (*a*) shows side views of pin main bodes having various shapes thereof, and FIG. 12 (*b*) the side views of the stop rings.

A pin main body 124 has a head portion and recessed groove 125 formed at the opposite end thereof (at the left end), while a pin main body 126 is formed with a tapered groove 127, and to those recessed groove 125 and the tapered groove 127 is applied a C ring 128 or an O ring 129 made of a soft material (such as a rubber), as a stop ring. Also, a pin main body 130 has an fitting or engagement structure with the member 42, which is formed with a small diameter portion 131 at the left end of the drawing, and a pin main body 132 has a joint structure by means of a screw and a screw groove 133 formed at the left end of the member 42.

According to the present embodiment, they can be disassembled and/or assembled, in the same manner as in the fitting structure mentioned above, thereby enabling easy rinsing and/or sterilization thereof.

Figure 13A:
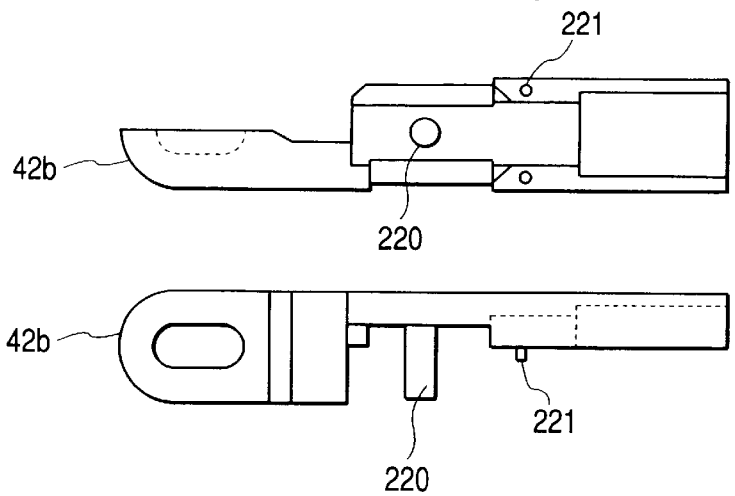
Figure 13B:
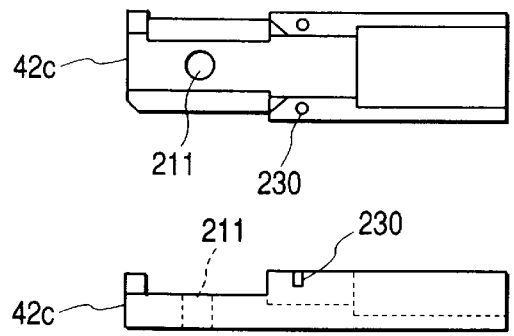
Figure 13C:
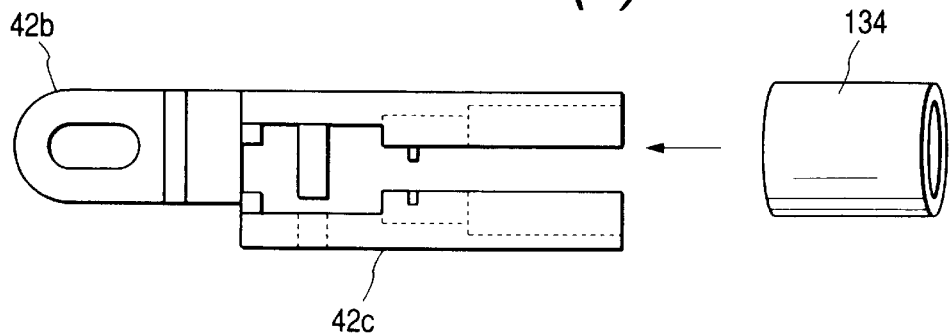
Figure 14A:
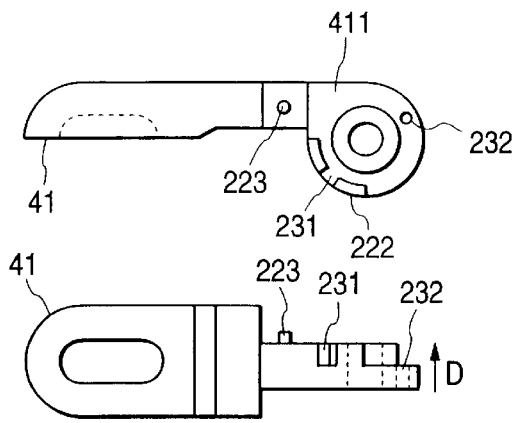
FIGS. 14 (*a*) to (*e*) show further other embodiment, in which a driving wire is fixed to a forceps member, according to the present invention.
Figure 14B:
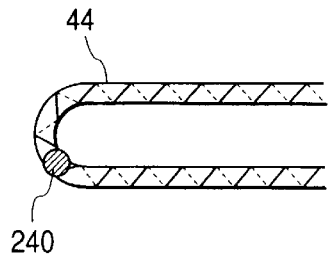
Figure 14C:
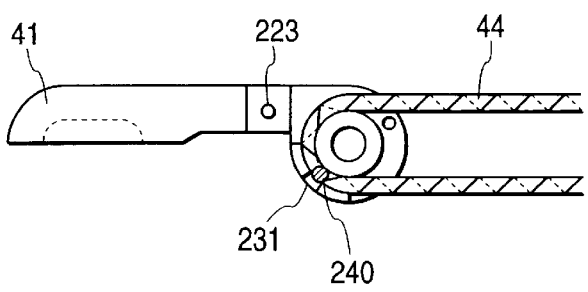
Figure 14D:
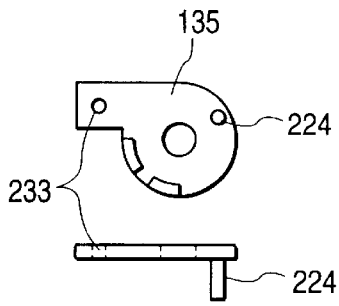
Figure 14E:
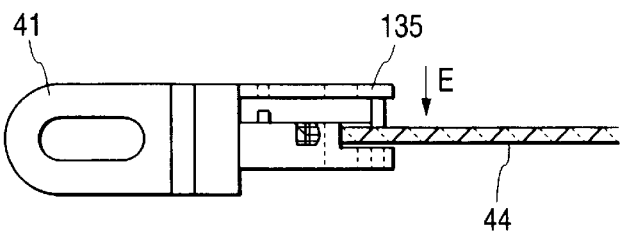

FIGS. 13 (*a*) to (*c*) show further other embodiment of the fixed forceps member. In the present embodiment, the member of the fixed forceps is divided into two (2) and the member of the movable forceps is inserted between the both members, thereby being constructing so that the constituent parts thereof are fixed by inserting a tube from an outside.

FIG. 13 (*a*) shows one of the fixed forceps member 42B which is divided into two (2) along with the axis from the tip to the back thereof, and in particular, an upper side portion of the figure shows the side view thereof, while a lower side portion the front plan view thereof. FIG. 13 (*b*) shows the other fixed forceps member 42C, and in particular, the upper side portion of the figure shows the front view thereof while the lower side the side view thereof. And, the FIG. 13 (*c*) shows an assembled structure view thereof.

The member 42B has a non-holding portion (the right-hand side portion in the figure) formed in a cylindrical shape, on an inner side of this are formed a projection 220 for use of a joint and a projection 221 for use of positioning. Also, the member 42C is formed in the cylindrical shape, and is formed with a bore 211 to be inserted with that projection 221, and a recess portion (or a bore) 230 to be engaged with the projection 221.

Those both members has such the structure that, as shown in the FIG. 13 (*c*), the projection 220 is fit into the bore 211 after inserting the member 41 of the FIG. 11 (*a*) thereto, while inserting the projection 221 into the recess portion 230, and finally the tube 134 is inserted from an outside in the direction of an arrow, thereby fixing the both members. Accordingly, the both members can be disassembled with ease, by means of attaching and/or detaching of the tube 134.

According to the present embodiment, they can be disassembled and/or assembled, in the same manner as in the embodiment mentioned above, thereby enabling easy rinsing and/or sterilization thereof.

FIGS. 14 (*a*) to (*e*) show further other embodiment, in which the driving wire is fixed onto the movable forceps member.

The FIG. 14 (*a*) shows a side view of the member of the movable forceps, in particular, in an upper side portion of the figure, while a front view thereof in a lower side thereof, the FIG. 14 (*b*) other embodiment of the driving wire, and the FIG. 14 (*c*) shows the condition where the driving wire is fixed onto a member of the movable forceps. The FIG. 6 (*d*) shows a fixing member for fixing the driving wire, and in particular, the upper side in the figure a top plan view while the lower side a side view thereof. And the FIG. 6 (*e*) shows an assembled structure view thereof.

As shown in the FIG. 14 (*a*), a projection 222 is formed around the outer periphery of the rotary portion 411 of the member 41 of the movable forceps, and on this projection 222 are formed a recess portion 231 for fixing the driving wire 44, a projection 223, and a recess portion 232 for use of positioning thereof. They are so constructed that, as shown in the FIG. 14 (*b*), a convex portion 240, such as a knot, etc., is formed on the driving wire 44, and as shown in the FIG. 14 (*c*), the convex portion 240 is fitted into the recess portion 231, so as to be wound around the rotary portion 441.

With this, the driving wire 44 will not come off even if stress is applied thereto. After that, the fixed member 135 having such the recess portion 233 and the projection 224 as shown in the FIG. 14 (*d*) are pushed into the direction of an arrow E in the FIG. 14 (*e*) to be fixed, thereby obtaining the forceps, which will not come off in the direction of an arrow D.

According to the present embodiment, in the same manner, they can be disassembled and/or assembled, thereby enabling easy rinsing and/or sterilization thereof.

Figure 15A:
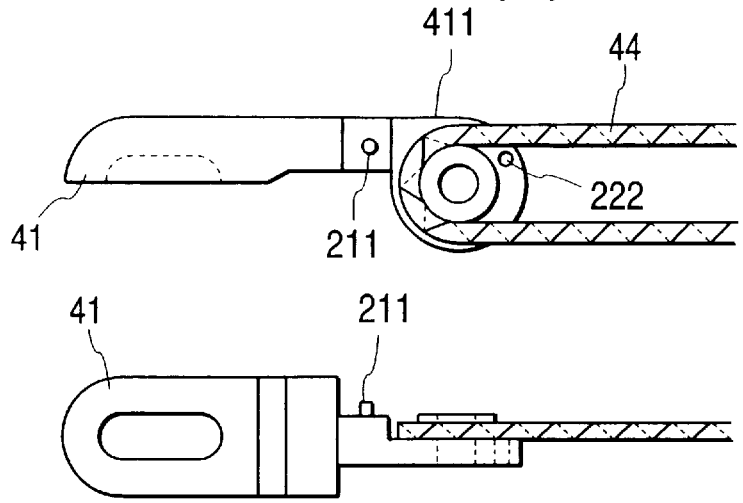
FIGS. 15 (*a*) to (*c*) also show further other embodiment, in which a driving wire is fixed to a forceps member, according to the present invention.
Figure 15B:
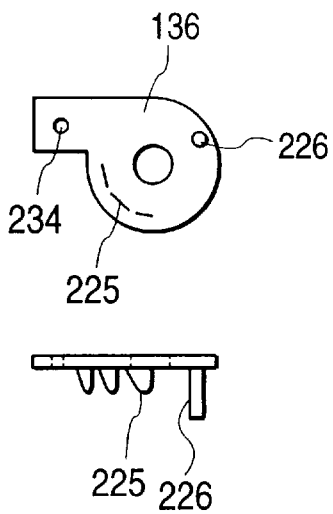
Figure 15C:
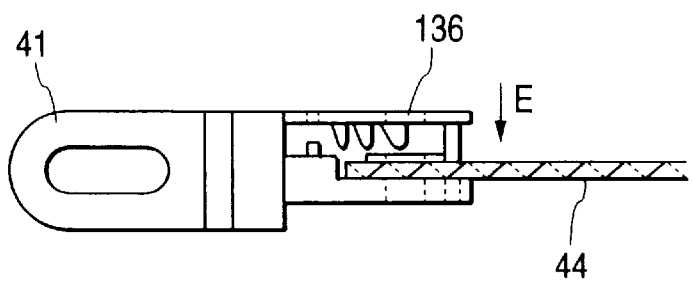

FIGS. 15 (a) to (c) show further other embodiment, in which the driving wire is fixed onto a member of the movable forceps.

FIG. 15 (a) shows, in particular, a side view of the member of the movable forceps, in particular in an upper side of the figure, while a front view thereof in a lower side, FIG. 15 (b), a top plan view of the fixed member, in particular in an upper side of the figure, while a side view thereof in a lower side, and FIG. 15 (c) shows the assembled structure thereof.

As shown in the FIG. 15 (a), the driving wire 44 is wound around the rotary portion 411 of the member 41 of the movable forceps. After that, a projection 225 formed in a shape of waves for holding down the driving wire 44, a recess portion 234 for use of positioning thereof, and a fixing member 136 having a recessed portion 234 and a projection 226, are pushed into the direction of an arrow E, as shown in the FIG. 15 (c), so as to fix the driving wire 44, thereby completing the assembling of the forceps.

According to the present embodiment, in the same manner, they can be disassembled and/or assembled, thereby enabling easy rinsing and/or sterilization thereof.

Figure 16A:
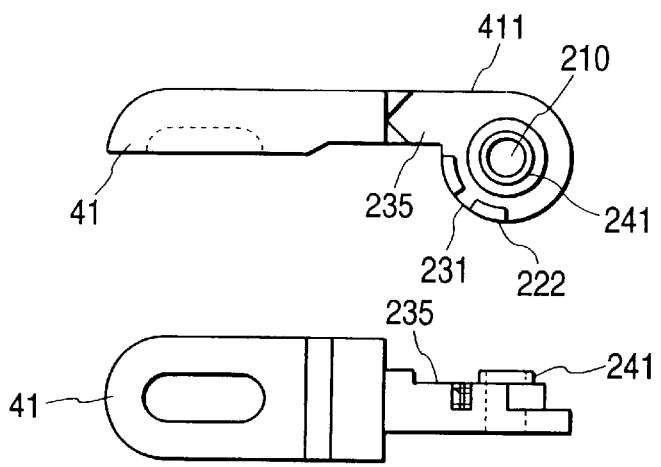
FIGS. 16 (*a*) to (*c*) also show further other embodiment, in which a driving wire is fixed to a forceps member, according to the present invention.
Figure 16B:
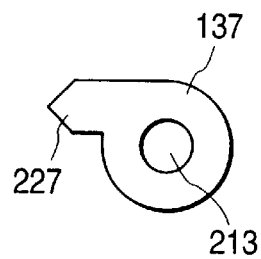
Figure 16C:
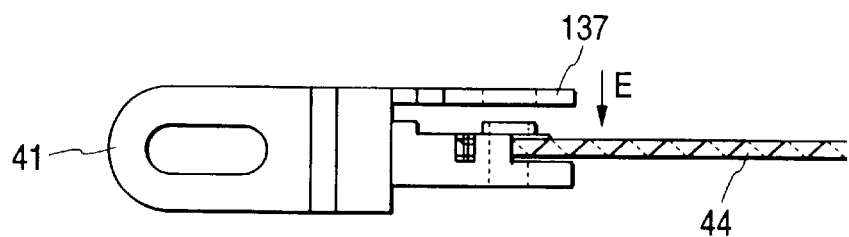
Figure 17A:
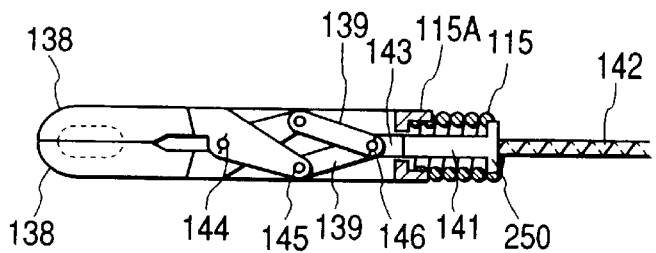
FIGS. 17 (*a*) to (*e*) shows further other embodiment of the forceps of a push-rod driving method, according to the present invention.
Figure 17B:
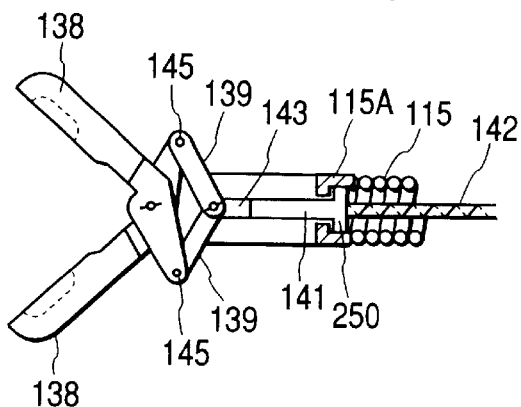
Figure 17C:
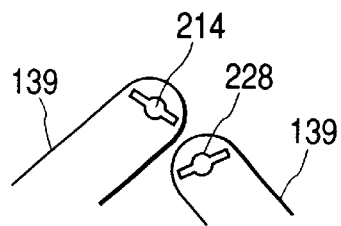
Figure 17D:
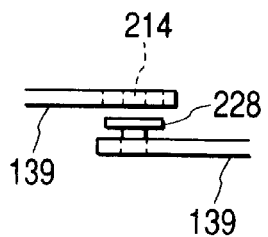
Figure 17E:
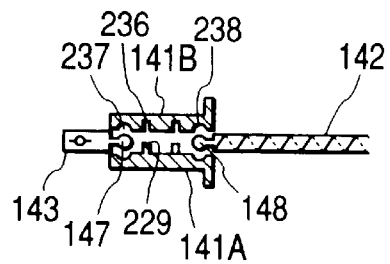

FIGS. 16 (a) to (c) show still further other embodiment, in which the driving wire is fixed onto a member of the movable forceps.

FIG. 16 (a) shows, in particular, a side view of the member of the movable forceps in an upper side of the figure, while a front plan view thereof in a lower side of the figure, FIG. 16 (b), in particular, a top plan view of the fixed member in an upper side of the figure, while a side view thereof in a lower side of the figure, and FIG. 16 (c) shows the assembled structure thereof.

As shown in the FIG. 16 (a), around the bore 210 on the rotary portion 411 is formed a convex portion 241 in a circle-like shape, while forming a recess portion 235 on a sliding surface in a shape of a triangle, directing to a tip of the member 41 of the movable forceps. After winding the driving wire 44 around the rotary portion 411, into the above-mentioned recess portion 235 shown in the FIG. 16 (b) is fitted the member 237 having a projection 227 and a bore 213, each having a triangle shape corresponding thereto, and the convex portion 241 is inserted into the bore 213 of the fixing member 137, thereby fixing the driving wire 44 by pushing it in the direction of the arrow E, as shown in the FIG. 16 (c).

According to the present embodiment, in the same manner, they can be disassembled and/or assembled, thereby enabling easy rinsing and/or sterilization thereof.

FIGS. 17 (a) to (e) shows an embodiment of the forceps mechanism of the push-rod driver method.

FIG. 17 (a) shows a side view in the condition where the forceps is closed, and FIG. 17 (b) a side view in the condition where the forceps is opened. The forceps of this push-rod drive method comprises: treatment members 138 for treating an objected portion, two (2) pieces of links 139, a connector 141 having a stopper 250, a rod 142, a link 143 for connecting between the above-mentioned link 139 and the connector 141, a hollow elastic member 115 attached onto a pedestal 115A which can be divided into two (2), etc., wherein the links 139 and 143 make up a link mechanism. Those parts are connected by means of the joint 144 connecting the treatment members 138 to each other, the joint 145 connecting between the treatment members 138 and the link 139, and the joint 146 connecting between two (2) pieces of the links 139 and the link 143, but freely rotating.

FIGS. 17 (c) and (d) show the details of the portion connecting the links to each other, in particular the FIG. 17 (c) shows a front plan view and the FIG. 17 (d) a side view thereof. At an end joint portion of the link 139 shown in the lower side of the drawing, a T-shape projection 228 is formed. Also, at one end joint portion of the link 139 shown in the upper side of the figure, a bore 214 is formed, corresponding to a head portion of the above-mentioned T-shape projection 228, and further the head portion of the T-shape projection 228 and the bore 214 are disposed at the positions, so that they can be engaged with each other under the condition that the link 139 is opened at an angle being equal to or larger than a predetermined value. In the same manner, the treatment members 138 and the links 139 are also disposed at the positions of the head portion and the link thereof, so that they can be engaged with each other under the condition that the treatment member 138 and the link 139 are opened at an angle being equal to or larger than a predetermined value (they will not come off when engaging at the predetermined angle). On a while, the stopper 250 of the connector 141 is provided at a position so that it will not come off because the treatment member 138 does not open up to a predetermined angle (90 degree) or more even under the condition where the rod 142 is pushed into at the maximum toward the left-hand direction. Further, since it differs at the respective joint portions, the predetermined angle defined between the projection and the bore is so determined that they will not come off when the forceps mechanism is operated. When being disassembled, the pedestal 115A is divided into to be detached, and the stopper 250 is shifted into the left-hand side direction in the figure, i.e., further to the left-hand side direction comparing to the position when they are not detached, therefore the joints 144, 145 and 146 can be taken away from the engagement thereof.

According to the present embodiment, in the same manner, they can be disassembled and/or assembled, thereby enabling easy rinsing and/or sterilization thereof.

FIG. 17 (e) shows a cross-section view of the connector portion for connecting between the rod and the link, and wherein the connector portion is detachable therefrom.

The connectors 141 have the fitting structure, so that they can be divided into two (2) along with the axial direction thereof from the tip (the left end in the drawing) to the back portion (the right end in the drawing), wherein a projection 229 is formed on the one portion of the connector 141A (the lower side in the drawing), and on the other portion of the connector 141B (the upper side in the drawing) is formed a recess portion 236, into which the above-mentioned projection 229 is inserted. Also, they have such the construction that, at the both ends of the upper and the lower connectors 141 are formed recess portions 236, respectively, into which the spherical portions 147 and 148 of, such as, the rod 142 and the link 143, so as to fix the rod 142 and the link 143 thereto.

According to the present embodiment, by dividing the connectors, it is possible to disassemble the rods, the links and the connectors, with ease.

As fully explained in the above, according to the present invention, it is possible to provide the forceps and the manipulator with using thereof, being small in the size and able to perform the open and close operation with a small curvature diameter.

Also, according to the present invention, the tension on the driving wire can be maintained at constant, to make the forceps open and close, even when it is bent at a small curvature diameter, therefore it is possible to prove the forceps and the manipulator with using thereof, being able to maintain the holding force at a constnt.

Further, according to the present invention, the forceps can be disassembled into and/or assembled from the parts constructing thereof, therefore rinsing and/or sterilizing can be performed thereon, easily.

While we have shown and described several embodiments in accordance with our invention, it should be understood that the disclosed embodiments are susceptible of changes and modifications without departing from the scope of the invention. Therefore, we do not intend to be bound by the details shown and described herein but intend to cover all such changes and modifications falling within the ambit of the appended claims.

What is claimed is:

1. A forceps, comprising:
   a pair of forceps members, being able to open or close at one end, so as to put an object between them, and being supported at the other end thereof;
   a driving wire for transferring tension thereon to one of said forceps members for bringing them to open and close in relation to each other; and
   a driver portion for giving the tension onto said driving wire, wherein:
   the one of said forceps members is built up with a member (A), being able to open or close at one end, so as to put the object between them, while being supported to freely rotate at the other end, and the other of said forceps members is built up with a member (B) which is supported fixedly at the other end;
   the driving wire is wound around a rotary portion at said other end of the member (A), and a portion of the wound portion thereof is fixed onto said rotary portion; and
   the tension for open and close operation is given from said driver portion to one end of the driving wire.

2. A forceps, as defined in the claim 1, wherein the position where said driving wire is fixed onto the rotary portion is set at a position, so that the driving wire remains on the rotary even if the member (A) opens at 90 degree to the member (B).

3. A forceps, comprising:
   a pair of forceps members, being able to open or close at one end, so as to put an object between them, and being supported at the other end thereof;
   a driving wire for transferring tension thereon to one of said forceps members for bringing them to open and close relative to each other; and
   a driver portion for giving the tension onto said driving wire, wherein:
   the one of said forceps members is built up with a member (A), being able to open or close at one end, so as to put the object between them, while being supported to freely rotate at the other end, and the other of said forceps members is built up with a member (B), which is supported fixedly at the other end;
   the driving wire is wound around a rotary portion at said other end of the member (A), and a portion of the wound portion thereof is fixed onto said rotary portion; and
   the driving wire is connected to the driver portion passing through an inside of a sheath.

4. A forceps, comprising:
   a pair of forceps members, being able to open or close at one end, so as to put an object between them, and being supported at the other end thereof;
   a driving wire for transferring tension thereon to one of said forceps members for bringing them to open and close relative to each other; and
   a driver portion for giving the tension onto said driving wire, wherein:
   the one of said forceps members is built up with a member (A), being able to open or close at one end, so as to put the object between them, while being supported to freely rotate at the other end, and the other of said forceps members is built up with a member (B) which is supported fixedly at the other end;
   the driving wire is wound around a rotary portion at said other end of the member (A), and a portion of the wound portion thereof is fixed onto said rotary portion;
   the driving wire is connected to the driver portion passing through an inside of a sheath, in which an elastic member lies therebetween;
   at a position of the elastic member is provided a means for separating the driving wire from an inner wall of the sheath; and
   the tension for open and close operation is given from the driver portion to the driving wire.

5. A forceps, as defined in the claim 4, wherein the means for separating said driving wire from the inner wall of the sheath is so constructed that, the driving wire passes through a bored sphere, on which a bore is formed, and a portion of the bored sphere comes to a hollow portion of the elastic member.

6. A forceps, as defined in claim 1, wherein a joint portion of said pair of forceps members is constructed to be detachable.

7. A forceps as defined in the claim 6, wherein the pair of forceps members are fitted at the joint portions thereof, through a lock and fitting structure by means of a pin, in said detachable structure.

8. A forceps as defined in the claim 6, wherein the pair of forceps members are fitted at the joint portions thereof, through a structure by means of a pin and a stop ring, in said detachable structure.

9. A manipulator, with using a forceps, comprising:
   a pair of forceps members, being able to open or close at one end, so as to put an object between them, and being supported at the other end thereof;
   a driving wire for transferring tension thereon to one of said forceps members for bringing them to open and close relative to each other; and
   a driver portion for giving the tension onto said driving wire, wherein said manipulator further comprising:
   a driving wire for performing a swing operation at a tip there; and
   a driver portion for giving a tension to the driving wire, wherein:
   the forceps is inserted in this manipulator;
   in this forceps, between said forceps members, the one of said forceps member is built up with a member (A), being able to open or close at one end, so as to put the object between them, while being supported to freely rotate at the other end; and the other of said forceps members is built up with a member (B) which is supported fixedly at the other end;
   the driving wire is wound around a rotary portion at said other end of the member (A), and a portion of the wound portion thereof is fixed onto said rotary portion; and the tension for open and close operation is given from said driver portion to one end of the driving wire.

10. A manipulator, with using a forceps, comprising:
a pair of forceps members, being able to open or close at one end, so as to put an object between them, and being supported at the other end thereof;
a driving wire for transferring tension thereon to one of said forceps members for bringing them to open and close relative to each other; and
a driver portion for giving the tension onto said driving wire, wherein said manipulator further comprises:
a driving wire for performing a swing operation at a tip there; and
a driver portion for giving a tension to the driving wire, wherein:
the forceps is inserted in this manipulator;
in this forceps, between said forceps members, the one of said forceps member is built up with a member (A), being able to open or close at one end, so as to put the object between them, while being supported to freely rotate at the other end; and the other of said forceps members is built up with a member (B) which is supported fixedly at the other end;
the driving wire is wound around a rotary portion at said other end of the member (A), and a portion of the wound portion thereof is fixed onto said rotary portion; and
the driving wire is connected to the driver portion passing through an inside of a sheath, in which an elastic member lies therebetween;
at a position of the elastic member is provided a means for separating the driving wire from an inner wall of the sheath; and
the tension for open and close operation is given from the driver portion to the driving wire.

11. A manipulator as defined in the claim 9, wherein a joint portion of said pair of forceps members is constructed to be detachable.

* * * * *